(12) United States Patent
Fukutani et al.

(10) Patent No.: US 8,260,403 B2
(45) Date of Patent: Sep. 4, 2012

(54) PHOTOACOUSTIC IMAGING APPARATUS AND PHOTOACOUSTIC IMAGING METHOD

(75) Inventors: Kazuhiko Fukutani, Yokohama (JP); Takao Nakajima, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 115 days.

(21) Appl. No.: 12/816,556

(22) Filed: Jun. 16, 2010

(65) Prior Publication Data
US 2010/0331662 A1 Dec. 30, 2010

(30) Foreign Application Priority Data

Jun. 26, 2009 (JP) ................................. 2009-152543

(51) Int. Cl.
*A61B 6/00* (2006.01)
(52) U.S. Cl. ...................................................... 600/476
(58) Field of Classification Search .......... 600/407–429, 600/473–480; 378/8, 19; 382/130–132; 356/432–445
See application file for complete search history.

(56) References Cited

U.S. PATENT DOCUMENTS

| | | | | |
|---|---|---|---|---|
| 6,426,990 | B1* | 7/2002 | Cesmeli | 378/8 |
| 7,525,661 | B2* | 4/2009 | Mandelis et al. | 356/432 |
| 2003/0002616 | A1* | 1/2003 | Cesmeli | 378/8 |
| 2003/0028098 | A1* | 2/2003 | Brock-Fisher | 600/431 |
| 2005/0175143 | A1* | 8/2005 | Miyazaki et al. | 378/19 |
| 2006/0235302 | A1* | 10/2006 | Grossman et al. | 600/443 |
| 2007/0083109 | A1* | 4/2007 | Ustuner et al. | 600/437 |
| 2007/0129627 | A1* | 6/2007 | Profio et al. | 600/407 |
| 2007/0232886 | A1* | 10/2007 | Camus et al. | 600/407 |
| 2008/0273778 | A1* | 11/2008 | Goto et al. | 382/131 |
| 2008/0285048 | A1* | 11/2008 | Chen et al. | 356/492 |
| 2008/0294150 | A1* | 11/2008 | Altshuler et al. | 606/3 |
| 2008/0306471 | A1* | 12/2008 | Altshuler et al. | 606/10 |
| 2009/0309895 | A1* | 12/2009 | Nagase et al. | 345/589 |
| 2011/0125017 | A1* | 5/2011 | Ramamurthy et al. | 600/443 |

OTHER PUBLICATIONS

M. Xu et al., "Universal Back-Projection Algorithm for Photoacoustic Computed Tomography", *Physical Review E*, vol. 71, 016706, pp. 016706-1-016706-7 (2005).
M. Xu et al., "Photoacoustic Imaging in Biomedicine", *Review of Scientific Instruments*, vol. 77, 042201, pp. 041101-1-041101-22 (2006).

* cited by examiner

*Primary Examiner* — Sanjay Cattungal
(74) *Attorney, Agent, or Firm* — Fitzpatrick, Cella, Harper & Scinto

(57) ABSTRACT

A photoacoustic wave detector detects a photoacoustic wave generated inside a specimen by light irradiated thereto. A signal processing device: forms first volume data from a first signal, the first signal being the detection signal acquired from the detector or a signal obtained by adjusting an amplitude of the detection signal; forms second volume data from a second signal, the second signal being a signal obtained by changing a phase of the first signal; forms third volume data from the first and second volume data; and generates and outputs image data representing information on an interior of the specimen from the third volume data.

7 Claims, 4 Drawing Sheets

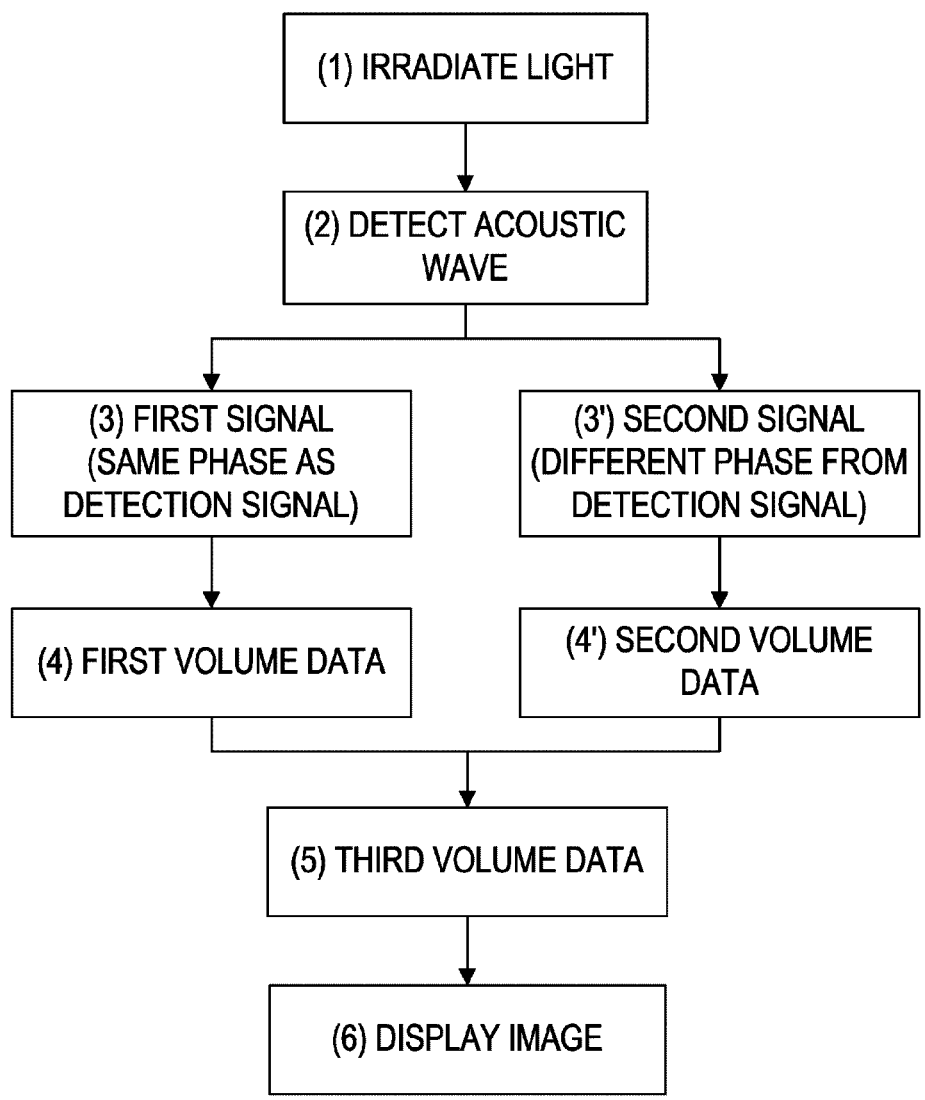

PHOTOACOUSTIC IMAGING APPARATUS AND PHOTOACOUSTIC IMAGING METHOD

BACKGROUND OF THE INVENTION

1. Field of the Invention

The present invention relates to a photoacoustic imaging method used in a photoacoustic imaging apparatus.

2. Description of the Related Art

The study of an optical imaging apparatus for obtaining information inside a specimen such as a living body by using the light irradiated from a light source such as a laser is actively advanced in medical fields. As one such optical imaging technique, there has been proposed photoacoustic tomography (PAT). Photoacoustic tomography is a technique in which acoustic waves generated from a living body (biological) tissue, which has absorbed the energy of light propagated and diffused in the interior of a specimen, are detected at a plurality of locations surrounding the specimen, and in which the signals thus obtained are subjected to mathematical analysis processing to visualize the information related to optical property values in the interior of the specimen. As a result of this, various information such as an initial pressure distribution, an optical energy absorption density distribution produced by light irradiation, etc., can be obtained, and these kinds of information can be applied to pinpointing the location of a malignant tumor accompanied by the multiplication of newly formed blood vessels, etc. The photoacoustic effect is a phenomenon in which, when pulsed light is shone on an object to be measured, an acoustic wave is generated due to the volume expansion in a region where the absorption coefficient is high inside the object to be measured. The acoustic wave generated due to the volume expansion by pulsed light irradiation is also called "a photoacoustic wave" in the present disclosure.

In general, in photoacoustic tomography, with respect to a specimen, at a variety of points on a closed spatial surface which encloses the entire specimen, in particular a spherical-shaped measurement surface, if the temporal change of an acoustic wave can be measured by the use of ideal sound detectors (of a wide band and point detection), an initial pressure distribution produced by light irradiation can be thoroughly reconstructed in a theoretical point of view. In addition, it is mathematically known that even in the case of a non-closed space, if measurement can be made in a cylindrical or planar manner with respect to the specimen, an initial pressure distribution produced by light irradiation can be substantially reconstructed (see Non-Patent Literature (NPL) 1).

The following equation (1) is a partial differential equation for PAT, and it is called a "photoacoustic wave equation". If this equation is solved, acoustic wave propagation from the initial pressure distribution can be described, so that it is possible to theoretically calculate in which places and in what manner an acoustic wave can be detected:

$$\left(\nabla^2 - \frac{1}{c^2}\frac{\partial^2}{\partial t^2}\right)p(r, t) = -p_0(r)\frac{\partial \delta(t)}{\partial t} \quad (1)$$

where r is location, t is time, p(r, t) is the temporal change of the sound pressure distribution, $p_0(r)$ is the initial pressure distribution, and c is the speed of sound. $\delta(t)$ is a delta function representing the shape of a light pulse.

On the other hand, an image reconstruction of PAT is to derive the initial pressure distribution $p_0(r)$ from the sound pressure $p_d(r_d, t)$ obtained at a detection point, and it is mathematically called an inverse problem. In the following, a universal back projection (UBP) method representatively used in the image reconstruction technique of PAT will be explained. In analyzing the photoacoustic wave equation in the form of equation (1) above on a frequency space, the inverse problem of calculating $p_0(r)$ can be solved in an accurate manner. The UBP represents the result thereof on a time space. The equation finally derived is as follows:

$$p_0(r) = -\frac{2}{\Omega_0}\nabla \cdot \int_{S_0} \vec{n}_0^S dS_0 \left[\frac{p_0(r_0, t)}{t}\right]_{t=|r-r_0|} \quad (2)$$

where $\Omega_0$ is the solid angle of an entire measuring area $S_0$ with respect to an arbitrary reconstruction voxel (or focus point). Moreover, transforming the equation plainly and simply results in the following equation:

$$p_0(r) = \int_{\Omega_0} b(r_0, t = |r - r_0|) \frac{d\Omega_0}{\Omega_0} \quad (3)$$

where $b(r_0, t)$ is projection data, and $d\Omega_0$ is the solid angle subtended by a detector area $dS_0$ with respect to an arbitrary observation point P. The initial pressure distribution $p_0(r)$ can be obtained by performing back projection of the projection data according to the integration of equation (3).

Here, note that $b(r_0, t)$ and $d\Omega_0$ are as follows:

$$b(r_0, t) = 2p(r_0, t) - 2t\frac{\partial p(r_0, t)}{\partial t} \quad (4)$$

$$d\Omega_0 = \frac{dS_0}{|r - r_0|^2}\cos\theta \quad (5)$$

where $\theta$ is an angle which is formed by the detector and the arbitrary observation point P. In the case where the distance between a sound source and a measuring point is large enough in comparison with the size of the sound source (acoustic far-field approximation), the following relation results:

$$p(r_0, t) << t\frac{\partial p(r_0, t)}{\partial t} \quad (6)$$

where $b(r_0, t)$ becomes as follows:

$$b(r_0, t) = -2t\frac{\partial p(r_0, t)}{\partial t} \quad (7)$$

Thus, in such an image reconstruction of PAT, it is known that the initial pressure distribution $p_0(r)$ can be calculated by obtaining projection data $b(r_0, t)$ by performing the time differentiation of the detection signal $p(r_0, t)$ acquired by the detector, and performing the back projection of the projection data thus obtained according to equation (3) (see NPL 1 and NPL 2).

[NPL1] *Physical Review E* 71, 016706 (2005)
[NPL2] *Review of Scientific Instruments*, 77, 041101 (2006)

SUMMARY OF THE INVENTION

However, equation (1), which is the photoacoustic wave equation used for calculating equation (3), assumes a constant speed of sound, measurements being made from all directions, impulsive photoexcitation, wide-band detection, point detection, and continuous sampling of an acoustic wave. In other words, if these above-mentioned assumptions do not hold, degradation arises in the image reconstructed. The following are basically raised as main causes of image deterioration: (1) the band limitation of the acoustic wave detector (incapability of dealing with acoustic waves of all frequencies); (2) the device element width of the acoustic wave detector; (3) the limited view; and (4) noise. It is known that a reduction in the resolution and contrast of a reconstructed image, and an increase in artifacts, will be caused by these factors. In particular, in the UBP method, a value proportional to the differential value of the detection signal is made use of as projection data, as shown in equation (7), so it is greatly affected by the influence of noise, etc., and an image obtained deteriorates to a large extent.

Accordingly, the present invention provides a photoacoustic imaging apparatus which is capable of reconstructing an image closer to an actual acoustic wave generation source distribution even under a condition that includes noise, etc., and is not ideal, by reconstructing the image without the use of the differential value of a detection signal.

The present invention in its first aspect provides a photoacoustic imaging apparatus including: a light source for irradiating a specimen with light; a detector that detects a photoacoustic wave generated inside the specimen by the light; and a signal processing device that images and outputs information on an interior of the specimen based on a detection signal acquired from the detector, wherein the signal processing device forms first volume data from a first signal, the first signal being the detection signal itself or a signal obtained by adjusting an amplitude of the detection signal, forms second volume data from a second signal, the second signal being a signal obtained by changing a phase of the first signal, forms third volume data from the first volume data and the second volume data, and generates output image data from the third volume data.

The present invention in its second aspect provides a photoacoustic imaging method used in a photoacoustic imaging apparatus, the method including the steps of: detecting, by means of a detector, a photoacoustic wave which is generated inside a specimen by light with which the specimen is irradiated; forming first volume data from a first signal, the first signal being a detection signal acquired from the detector or a signal obtained by adjusting an amplitude of the detection signal; forming second volume data from a second signal, the second signal being a signal obtained by changing a phase of the first signal; forming third volume data from the first volume data and the second volume data; and generating and outputting, from the third volume data, image data which represents information on an interior of the specimen.

The present invention in its third aspect provides a non-transitory computer readable medium storing a program for causing a computer to perform a method comprising the steps of: acquiring a detection signal of a photoacoustic wave which is generated inside a specimen by light irradiated thereto; forming first volume data from a first signal, the first signal being the detection signal acquired or a signal obtained by adjusting an amplitude of the detection signal; forming second volume data from a second signal, the second signal being a signal obtained by changing a phase of the first signal; forming third volume data from the first volume data and the second volume data; and generating and outputting, from the third volume data, image data which represents information on an interior of the specimen.

According to the present invention, by reconstructing an image without the use of the differential value of a detection signal, it is possible to reconstruct the image closer to an actual acoustic wave generation source distribution even under a condition that is not ideal, including noise, etc.

Further features of the present invention will become apparent from the following description of exemplary embodiments with reference to the attached drawings.

BRIEF DESCRIPTION OF THE DRAWINGS

FIG. 2 is a flow chart showing one example of an image construction method according to the present invention.

DESCRIPTION OF THE EMBODIMENTS

Figure 1:
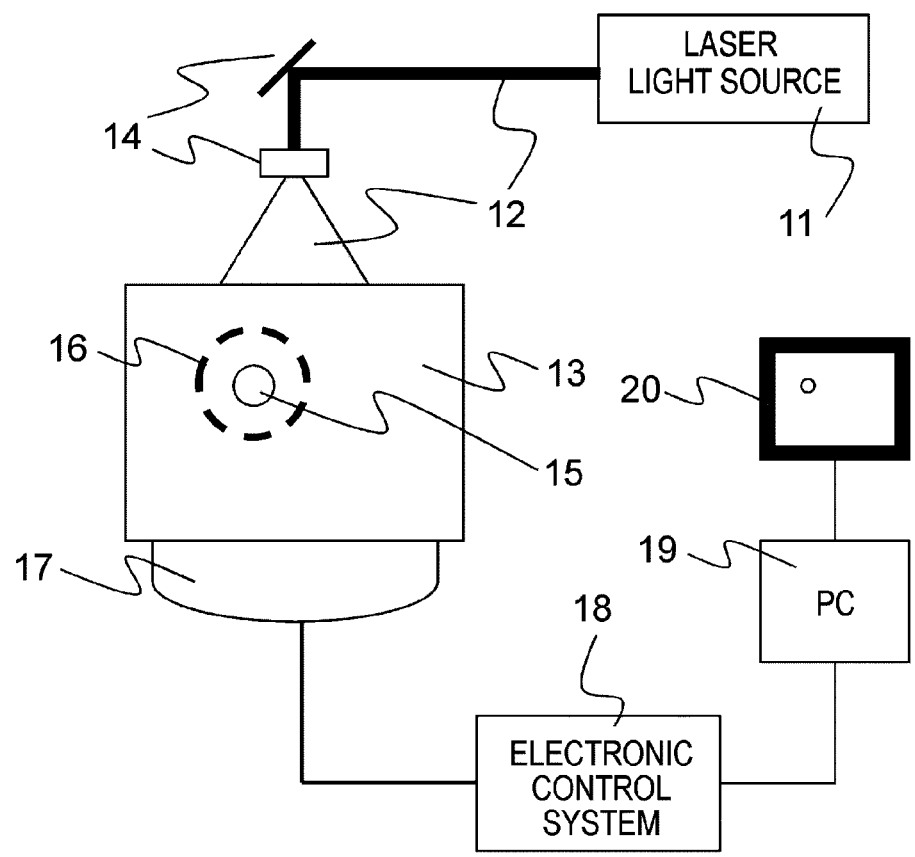
FIG. 1 is a schematic diagram showing an example of the construction of a photoacoustic imaging apparatus according to one embodiment of the present invention.

Hereinafter, reference will be made to a preferred embodiment of the present invention, while referring to the accompanying drawings. FIG. 1 shows an example of the construction of a photoacoustic imaging apparatus to which a photoacoustic imaging method of the present invention can be applied. The photoacoustic imaging apparatus is to make it possible to image biological information for the purposes of diagnosing malignant tumors, blood vessel diseases, etc., observing the progress of a chemical treatment, etc. In the present invention, biological information is a source distribution of an acoustic wave produced by light irradiation, which includes an initial pressure distribution in a living body or an optical energy absorption density distribution derived therefrom, and a concentration distribution of the substances which constitute a living body (biological) tissue, obtained from those pieces of information. For example, the concentration distribution of substances is the degree of oxygen saturation, etc.

The photoacoustic imaging apparatus is composed of a light source 11, an optical device 14, an acoustic wave detector (also referred to as a probe) 17, an electronic control system 18, a signal processing device 19, and a display device 20. The light source 11 is a device that emits light 12. The optical device 14 is an optical system that is composed of, for example, lenses, mirrors, optical fibers, etc. The light 12 emitted from the light source 11 is guided by the optical device 14, so that it is irradiated on a specimen 13 such as a living body. When a part of the energy of the light transmitted through the interior of the specimen 13 is absorbed by a light absorber 15 such as a blood vessel, etc., an acoustic wave (typically, ultrasonic wave) 16 is generated from the light absorber 15. This is a photoacoustic wave. The acoustic wave detector 17 detects the acoustic wave 16 generated from the light absorber 15, and converts it into an electrical signal. The electronic control system 18 is a control unit that performs amplification, digital conversion, etc., of the electrical signal outputted from the acoustic wave detector 17. The signal processing device 19 is an apparatus that performs the imaging (i.e., generating image data) of the information on the interior of the specimen based on a digital signal (detection signal) outputted from the electronic control system 18, and outputs the image data to the display device 20. The signal processing device 19 is composed of, for example, a personal computers (PC). The display device 20 is a device that displays an image.

The acoustic wave 16 is generated by thermal expansion from the light absorber 15 in the interior of the living body, by using, as the light 12 irradiated to the specimen, pulsed light or the like with its energy changing in a continuous manner. This is because the temperature of the light absorber 15 is raised due to its absorption of the pulsed light, so that the volume expansion thereof is caused to occur by the temperature rise, thereby generating an acoustic wave. It is preferable that the pulse width of the light at this time be set to such an extent that a heat stress confinement condition can be applied so as confine the absorbed energy within the light absorber 15 in an efficient manner. Typically, the pulse width ranges from about several nanoseconds to about several tens of nanoseconds.

Next, reference will be made to the flow of the photoacoustic imaging method by the use of a flow chart in FIG. 2. (1) First, pulsed light is irradiated from the light source 11 to the specimen 13. (2) The acoustic wave 16 generated in the interior of the specimen by light irradiation is detected by the acoustic wave detector 17, and is converted into a digital signal by means of the electronic control system 18. (3) The signal processing device 19 generates a first signal from the detection signal acquired in (2). The first signal may be the detection signal itself, or may be a signal obtained by adjusting the amplitude of the detection signal. The phase characteristics of the detection signal and the first signal should at least be the same (i.e., the phases of the individual frequency components are in agreement with each other). (4) The signal processing device 19 forms first volume data by the use of the first signal as projection data. Any method including well-known conventional ones may be used for conversion from the projection data to volume data. (3') On the other hand, the signal processing device 19 generates a second signal by changing the phase of the first signal. For example, the signal processing device 19 obtains the second signal, which is a signal in a time domain, by first frequency-resolving the first signal by means of Fourier transform and changing the phase of each frequency component, and then performing inverse Fourier transform thereon. In other words, the second signal is a signal which has the same amplitude characteristic as that of the first signal but has a phase characteristic different from that of the first signal. (4') The signal processing device 19 forms second volume data by the use of the second signal as projection data. (5) The signal processing device 19 forms third volume data from the first and the second volume data. For example, the square root of the sum of squares (Root Sum Square) of the first and the second volume data, or the sum of the absolute values thereof, or a value proportional to them, can be used as a voxel value of the third volume data. Alternatively, the third volume data may be calculated as the arithmetic mean or the geometric mean of the first and the second volume data. (6) The signal processing device 19 generates final output image data from the third volume data, and outputs it to the display apparatus 20.

In (3) of FIG. 2, it is preferable that the signal processing device 19 adjust the amplitude of the detection signal so as to correct the diffraction and/or attenuation of an acoustic wave. For example, the detection signal multiplied by a coefficient proportional to the time from the irradiation of light until the detection (reception) of an acoustic wave can be used as the first signal. The acoustic wave generated is decreased in energy density in proportion to the distance of propagation thereof, due to the superposition of spherical waves. Thus, it is possible to offset the attenuation of the acoustic wave by carrying out the multiplication of the coefficient corresponding to the reception time of the acoustic wave detector, as stated above.

In addition, in (3'), it is preferable that the signal processing device 19 generate the second signal by delaying the phase of a positive frequency component included in the first signal by 90 degrees, and at the same time by advancing the phase of a negative frequency component included in the first signal by 90 degrees. Here, note that the second signal shown herein is equivalent to the Hilbert transform of the first signal.

Figure 3A:
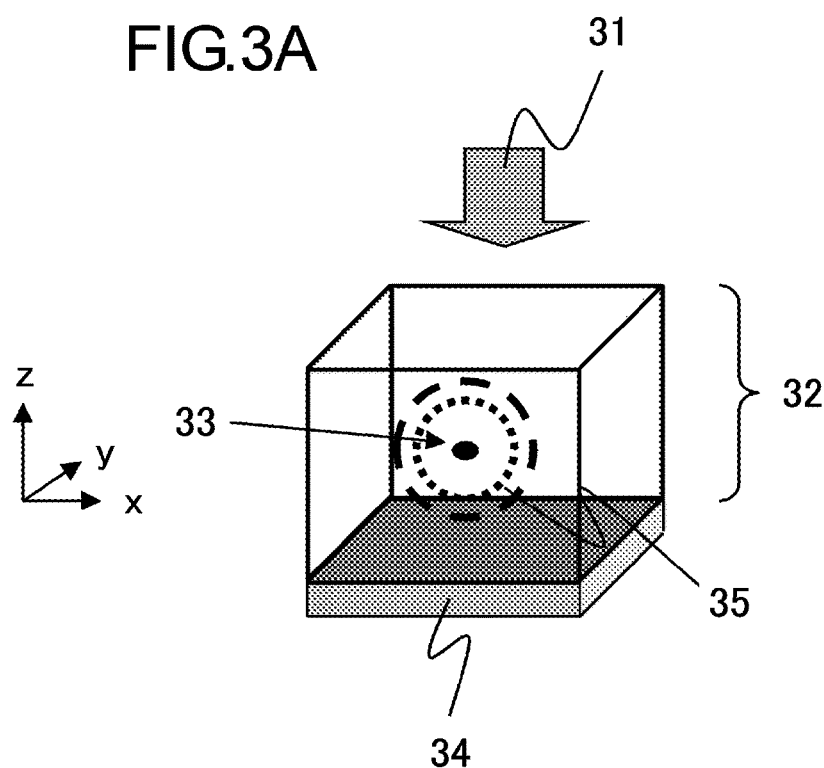
FIG. 3A is a view showing an experimental model.
Figure 3B:
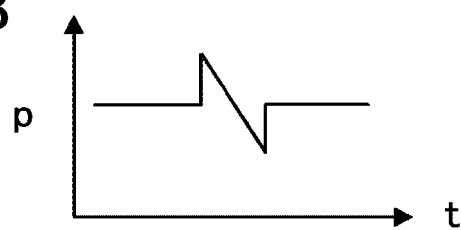
FIG. 3B is a view showing an example of a detection signal.
Figure 3C:
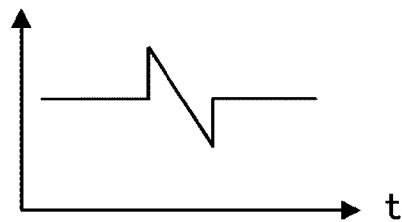
FIG. 3C is a view showing one example of a first signal.
Figure 3D:
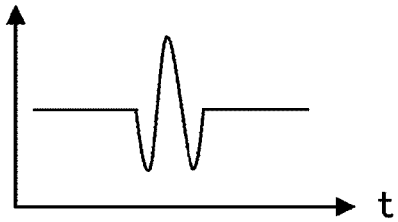
FIG. 3D is a view showing one example of a second signal.

FIG. 3A shows an experimental model, and FIG. 3B through FIG. 3D show examples of signals obtained by light irradiation. As shown in FIG. 3A, a specimen 32 is irradiated with light 31, and an acoustic wave 35 generated from a light absorber 33 in the specimen is detected by an acoustic wave detector 34. Here, for the sake of simplicity, it is assumed that the light absorber 33 is a spherical body, and further, the entire spherical body absorbs light in a uniform manner. In addition, it is also assumed that the acoustic wave detector 34 is of an array type having a plurality of sensing elements arranged in a two-dimensional fashion, and is installed on a surface which is arranged in opposition to a light irradiation surface. Under these assumptions, a detection signal detected by a certain sensing element becomes an N type signal which takes an N shape, as shown in FIG. 3B (wherein the axis of abscissa is time and the axis of ordinate is sound pressure). Here, note that a photoacoustic signal observed in an actual system is the convolution of an impulse response of the acoustic wave detector reflecting the bandwidth and magnitude thereof to the N type signal, but it is omitted here for the purpose of simplification. In addition, the time width of this N type signal is the diameter of the light absorber 33 divided by the speed of sound, and the time width between the center of the N type signal and the time point of light irradiation is equal to the distance between the location of that sensing element and the center position of the light absorber divided by the speed of sound. FIG. 3C shows the first signal. The first signal has the same phase characteristic as that of the detection signal (i.e., the first signal has the same or similar waveform as that of the detection signal). FIG. 3D shows the second signal obtained by carrying out the Hilbert transform of the first signal. In cases where the first signal is an N type signal, there is obtained the second signal which has a waveform in which the central portion of the N type signal becomes positive and the both end portions thereof become negative.

Figure 4:
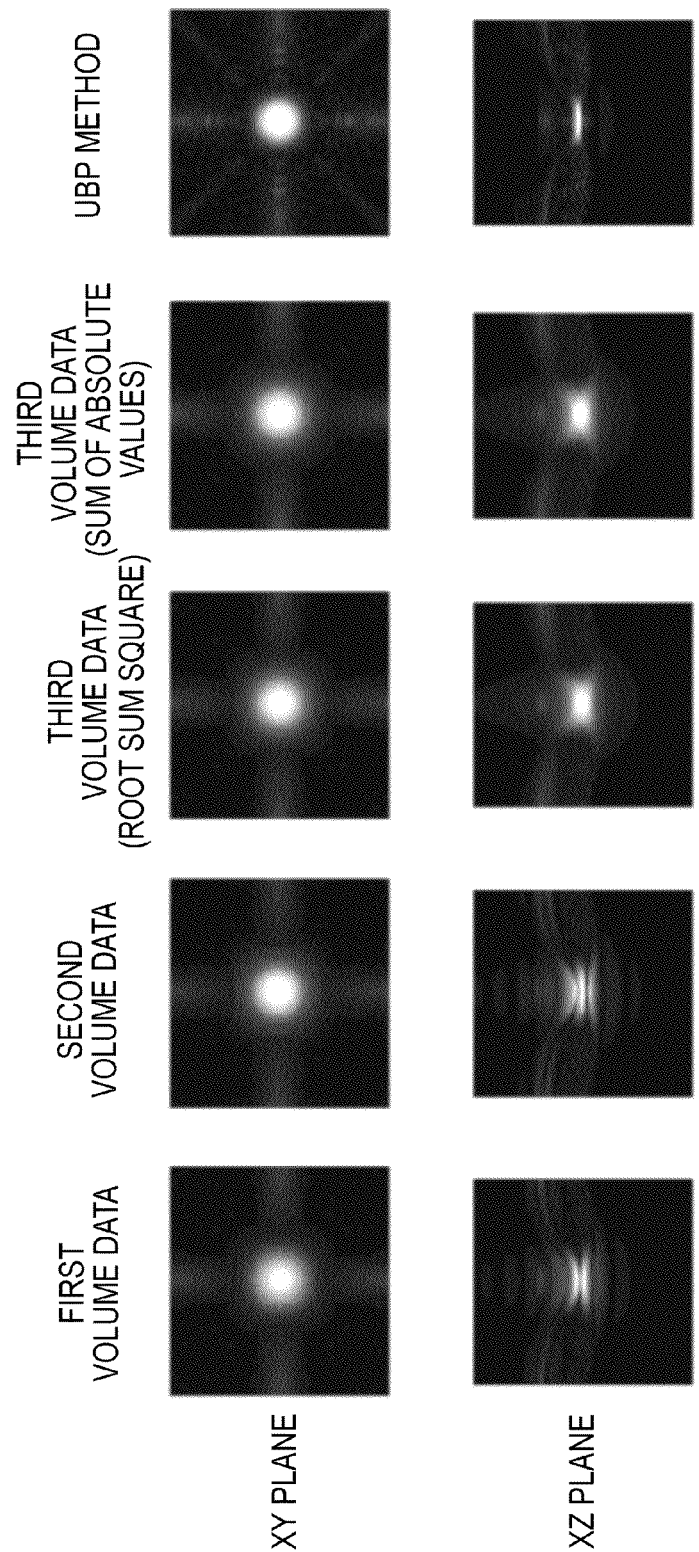
FIG. 4 is examples of volume data images obtained according to the method of the present invention and a conventional UBP method, respectively.

FIG. 4 is examples of volume data obtained from a signal measured in the model shown in FIG. 3A. Here, note that in order to take into consideration the influence of an element width in the acoustic wave detector 34, an acoustic wave was detected with an element size of 2 mm×2 mm and an array of elements of 18×18. Images in an upper part of FIG. 4 are MIP (Maximum Intensity Projection) images of the volume data as seen from an XY plane, i.e., images which are formed by projecting the maximum contrast in a Z direction of the volume data on the XY plane. Images in a lower part of FIG. 4 are MIP images of the volume data as seen from an XZ plane. FIG. 4 shows, in order from the left to the right, the first volume data, the second volume data, one kind of third volume data (the square root of the sum of squares), another kind of third volume data (the sum of absolute values), and volume data based on a general UBP method. In the examples of FIG. 4, the first volume data is calculated by substituting the first signal for the projection data of equation (3). The same is true of the second volume data. However, the back projection method cannot be limited to the method shown in expression (3), but any methods well-known in the art, such as the Fourier transform method or a filtered back projection method using the Radon transform, can be used.

The one third volume data (the square root of the sum of squares) is the square root of the sum of the square of the voxel value of the first volume data and the square of the voxel value (voxel data) of the second volume data. Also, the another third volume data (the sum of absolute values) is the sum of the absolute value of the voxel value of the first volume data and the absolute value of the voxel value of the second volume data.

It can be seen that an image closer to a spherical shape is obtained with both of the third volume data as compared with the volume data in the conventional UBP method. In addition, though it is difficult to determine from FIG. 4, the influence of an artifact generated from the spherical body in a radial manner becomes smaller in both of the third volume data rather than the volume data in the UBP method. It is considered that such an enhancement of image quality is based on the following reasons. Firstly, the differential value of the detection signal is not used for the calculation of the volume data, so it is unlikely to be affected by the influence of high frequency noise. Secondly, the first and the second volume data formed from different signals, respectively, show different artifacts, so by synthesizing these artifacts, it is possible to relatively reduce the artifacts.

Next, this embodiment of the present invention will be described in a specific manner.

In FIG. 1, the light source 11 is intended to irradiate the light of a specific wavelength to be absorbed by a specific component among those components which make up the living body. However, the light source may be formed integrally with the photoacoustic imaging apparatus of the present invention, or the light source may be formed separately therefrom as a different unit. As the light source, there is provided at least one pulsed light source that can generate pulsed light with a pulse width on the order of from several nanoseconds to several hundreds nanoseconds. Here, note that in cases where the sound pressure of the acoustic wave to be detected may be small, light of which the intensity (energy) changes over time, such as a sine wave, etc., should be used instead of the pulsed light of the above-mentioned order. A laser capable of obtaining a large output is desirable as the light source, but it is also possible to use a light emitting diode or the like instead of the laser. As the laser, there can be used various types of lasers such as a solid-state laser, a gas laser, a dye laser, a semiconductor laser, and so on. The timing of irradiation, the waveform, the intensity, etc., of the laser are controlled by the signal processing device 19 or an unillustrated control unit.

Here, note that in this embodiment, an example using a single light source as the light source 11 is shown, but a plurality of light sources can instead be used. In that case, in order to raise the irradiation intensity of light to be irradiated on the living body, there can be used two or more light sources which oscillate at the same wavelength, or in order to measure differences in the optical property distributions according to the wavelengths, two or more light sources having different oscillation wave lengths can be used. Here, note that if a dye of which the oscillating wavelength is convertible, OPO (Optical Parametric Oscillators), or crystals of titanium sapphire and alexandrite can be used as the light source 11, it will also become possible to measure the differences in the optical property distributions depending upon the wavelengths. With respect to the wavelength of the light source to be used, it is preferably in a range of from 700 nm to 1,100 nm, in which the absorption of optical energy in the living body is small. However, in cases where an optical property distribution of a living body tissue relatively near a surface of the living body is obtained, it is also possible to use a wavelength range, such as for example a range of from 400 nm to 1,600 nm, wider than the above-mentioned wavelength range.

It is also possible to make the light 12 irradiated from the light source(s) 11 propagate by the use of an optical waveguide or the like. As the optical waveguide, an optical fiber is preferable. In the case of using an optical fiber, it is also possible to guide light to the surface of the living body by the use of a plurality of optical fibers for the individual light sources, respectively, or light beams from the plurality of light sources may be led to a single optical fiber, so that all the light beams can be guided to the living body by using only the single optical fiber. The optical device 14 is such as, for example, mirrors that reflect light, lenses that condense and expand light or change the shape of light, or the like. As such optical components, anything can be used that is able to irradiate the light 12 emitted from the light source(s) to the specimen 13 in a desired shape. Here, note that in general, it is more preferable for lenses to expand the light into a certain amount of area than to make it be condensed. In addition, it is preferable that a region in which the specimen is irradiated be movable. In other words, the photoacoustic imaging apparatus of the present invention is preferably constructed such that the light generated from the light source is able to move on the specimen. Due to such a light movable construction, it is possible to irradiate the light to a much larger area. Also, it is still more preferable that the region in which the light is irradiated on the specimen (i.e., the light irradiated on the specimen) be able to move in synchronization with the acoustic wave detector 17. As a method for moving the region in which the light is irradiated on the specimen, there are a method using movable mirrors or the like, a method of moving the light source itself in a mechanical manner, etc.

The photoacoustic imaging apparatus of the present invention is intended to make the diagnosis of malignant tumors, blood vessel diseases of humans and/or animals, the progress observation of a chemical treatment, and so on. Therefore, as the specimen 13, an object to be diagnosed such as a breast, a finger, a limb (hand, foot), etc., of a human body or an animal, etc., is assumed. Also, as the light absorber 15, there can be applied or used those which exhibit a high absorption coefficient within the specimen, and if a human body is an object to be measured, for example, the light absorber corresponds to oxidized or reduced hemoglobin, a blood vessel containing a lot of oxidized or reduced hemoglobin, or a malignant tumor including a lot of newborn blood vessels. In addition, a contrast medium introduced from the outside of the specimen can also be used as the light absorber.

The acoustic wave detector 17 is composed of a transducer using a piezo-electric phenomenon, a transducer using the resonance of light, a transducer using the change of capacitance, or the like. Any kind of acoustic wave detector can be used as long as it is able to detect an acoustic wave. The acoustic wave detector 17 in the photoacoustic imaging apparatus of the present invention preferably has a plurality of sensing elements arranged in a two-dimensional manner. By using such a two-dimensional array device, it is possible to detect an acoustic wave at a plurality of places at the same time, whereby the detection time can be shortened, and the influence of the vibration of the specimen, etc., can be reduced. Also, it is desirable to use an acoustic impedance matching agent, though not illustrated, such as gel, water or the like for suppressing the reflection of sonic waves, which is arranged between the acoustic wave detector 17 and the specimen.

The electronic control system 18 amplifies the electrical signal obtained from the acoustic wave detector 17, and converts it from an analog signal into a digital signal. The signal processing device 19 generates the above-mentioned first signal and second signals from the measurement data (the detection signal) obtained from the electronic control system 18, and converts those signals into image data (volume data) with an optical property distribution. The signal processing device 19 can be composed, for example, of a computer that is provided with a CPU (central processing unit), a main storage (memory), an auxiliary storage (hard disk, etc.), an input device, and so on. A program for achieving the function of the signal processing device 19 is stored in the auxiliary storage of the computer. The CPU loads the program into the main storage from the auxiliary storage and executes it, so that processing steps (3) through (6) in FIG. 2 are executed, and data analysis of the measurement data is carried out. Here, note that as a data analysis technique (an image reconstruction technique), there can be used a filtered back projection method, a Fourier transform method, a spherical Radon transform method, a synthetic aperture method, etc., all of which are used in ordinary or conventional photoacoustic tomography. As the display device 20, anything can be used if it can display image data created by the signal processing device 19. For example, a liquid crystal display or the like can be used.

Here, note that in the case of using light of a plurality of wavelengths, an absorption coefficient distribution inside the specimen is calculated with respect to each wavelength by means of the above-mentioned system. Then, by comparing the values thus calculated with the wavelength dependency specific to substances (glucose, collagen, oxidized and reduced hemoglobin, etc.) which constitute the living body tissue, it is also possible to create, as image data, a concentration distribution of the substances constituting the living body.

Aspects of the present invention can also be realized by a computer of a system or apparatus (or devices such as a CPU or MPU or GPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., non-transitory computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-152543, filed on Jun. 26, 2009, which is hereby incorporated by reference herein in its entirety.

What is claimed is:

1. An in vivo photoacoustic imaging apparatus comprising:
a detector configured to detect a photoacoustic wave generated inside a specimen by irradiating the specimen with light; and
a signal processing device that images and outputs information on an interior of the specimen based on a detection signal acquired from said detector,
wherein said signal processing device
forms first volume data from a first signal, the first signal being the detection signal itself or a signal obtained by adjusting an amplitude of the detection signal,
generates a second signal by changing a phase of the first signal,
forms second volume data from the second signal,
forms third volume data from the first volume data and the second volume data, and
generates output image data from the third volume data.

2. The photoacoustic imaging apparatus according to claim 1, wherein said signal processing device generates the second signal by delaying a phase of a positive frequency component contained in the first signal by 90 degrees and advancing a phase of a negative frequency component contained in the first signal by 90 degrees.

3. The photoacoustic imaging apparatus according to claim 1, wherein said signal processing device generates the first signal by multiplying the detection signal by a coefficient proportional to a period of time from the irradiation of the specimen with light until the detection of the photoacoustic wave.

4. The photoacoustic imaging apparatus according to claim 1, wherein the third volume data has a value proportional to a square root of a sum of squares of the first volume data and the second volume data.

5. The photoacoustic imaging apparatus according to claim 1, wherein the third volume data has a value proportional to a sum of absolute values of the first volume data and the second volume data.

6. An in vivo photoacoustic imaging method used in a photoacoustic imaging apparatus, the method comprising the steps of:
detecting, by means of a detector, a photoacoustic wave which is generated inside a specimen by light irradiated thereto;
forming first volume data from a first signal, the first signal being a detection signal acquired from the detector or a signal obtained by adjusting an amplitude of the detection signal;
generating a second signal by changing a phase of the first signal,
forming second volume data from the second signal;
forming third volume data from the first volume data and the second volume data; and
generating and outputting, from the third volume data, image data which represents information on an interior of the specimen.

7. A non-transitory computer readable storage medium storing, in executable form, a program for causing a computer to perform an in vivo method comprising the steps of:
acquiring a detection signal of a photoacoustic wave which is generated inside a specimen by light irradiated thereto;
forming first volume data from a first signal, the first signal being the detection signal acquired or a signal obtained by adjusting an amplitude of the detection signal;
generating a second signal by changing a phase of the first signal,
forming second volume data from the second signal;
forming third volume data from the first volume data and the second volume data; and
generating and outputting, from the third volume data, image data which represents information on an interior of the specimen.

* * * * *